(12) United States Patent
Pang et al.

(10) Patent No.: US 11,458,062 B2
(45) Date of Patent: Oct. 4, 2022

(54) MOTION STABILIZING DEVICE FOR A COSMETIC APPLICATOR

(71) Applicant: L'Oreal, Paris (FR)

(72) Inventors: Christopher Pang, New York, NY (US); Thomas Stephen Kearney, II, Scotch Plains, NJ (US); Oliver Jiren Sha, Fort Lee, NJ (US); Kyoo Jin Park, Leonia, NJ (US); Vishal Pandya, Metuchen, NJ (US); Zane Miller, Seattle, WA (US); Edmond Irizarry, Dayton, MN (US)

(73) Assignee: L'Oreal, Paris (FR)

( * ) Notice: Subject to any disclaimer, the term of this patent is extended or adjusted under 35 U.S.C. 154(b) by 626 days.

(21) Appl. No.: 16/133,969

(22) Filed: Sep. 18, 2018

(65) Prior Publication Data

US 2020/0085168 A1 Mar. 19, 2020

(51) Int. Cl.
| | | |
|---|---|---|
| *A61F 4/00* | (2006.01) |
| *A61H 1/02* | (2006.01) |
| *G01P 13/00* | (2006.01) |
| *G06K 7/10* | (2006.01) |
| *G06K 19/077* | (2006.01) |

(Continued)

(52) U.S. Cl.
CPC .......... *A61H 1/0285* (2013.01); *A61B 5/1101* (2013.01); *A61F 4/00* (2013.01); *A61H 1/00* (2013.01); *G01P 13/00* (2013.01); *G06K 7/10366* (2013.01); *G06K 19/07758* (2013.01); *A45D 34/04* (2013.01); *A61H 2201/0153* (2013.01); *A61H 2201/0157* (2013.01); *A61H 2201/0165* (2013.01); *A61H 2201/5058* (2013.01); *A61H 2201/5084* (2013.01)

(58) Field of Classification Search
CPC ....................................................... A61F 4/00
See application file for complete search history.

(56) References Cited

U.S. PATENT DOCUMENTS

| | | | | |
|---|---|---|---|---|
| 52,275 | A * | 1/1866 | Dummer ................. | B30B 9/321 100/245 |
| 6,553,161 | B1 * | 4/2003 | Upton .................. | G02B 6/4225 385/25 |

(Continued)

FOREIGN PATENT DOCUMENTS

| | | |
|---|---|---|
| EP | 3 120 767 A1 | 1/2017 |
| JP | 2017-23752 A | 2/2017 |
| WO | WO 2006/020577 A2 | 2/2006 |

OTHER PUBLICATIONS

International Search Report and Written Opinion dated Mar. 11, 2020, in PCT/US2019/061489, 13 pages.

(Continued)

*Primary Examiner* — Jacqueline Woznicki
(74) *Attorney, Agent, or Firm* — Oblon, McClelland, Maier & Neustadt, L.L.P.

(57) ABSTRACT

An apparatus is provided that stabilizes an applicator in response to the motion caused by a user, comprising: a receiver configured to be coupled with a cosmetic applicator; at least one sensor configured to detect a movement caused by a user; circuitry configured to determine a compensation movement to offset the detected movement; and at least one motion generation device embedded in the receiver configured to control a motion of the cosmetic applicator according to the determined compensation movement.

5 Claims, 11 Drawing Sheets

(51) Int. Cl.
*A61H 1/00* (2006.01)
*A61B 5/11* (2006.01)
*A45D 34/04* (2006.01)

(56) References Cited

U.S. PATENT DOCUMENTS

| | | | | |
|---|---|---|---|---|
| 8,494,507 | B1* | 7/2013 | Tedesco | G09B 21/009 |
| | | | | 455/418 |
| 10,159,428 | B1* | 12/2018 | Shoeb | A61B 5/7275 |
| 10,159,432 | B1* | 12/2018 | Pathak | A61B 5/1125 |
| 10,264,971 | B1* | 4/2019 | Kennedy | A61B 5/6829 |
| 2006/0032512 | A1 | 2/2006 | Kress et al. | |
| 2009/0007928 | A1 | 1/2009 | Kress et al. | |
| 2009/0007929 | A1 | 1/2009 | Kress et al. | |
| 2010/0228362 | A1* | 9/2010 | Pathak | A61F 4/00 |
| | | | | 623/65 |
| 2013/0297022 | A1* | 11/2013 | Pathak | A61B 5/1101 |
| | | | | 623/14.13 |
| 2014/0052275 | A1* | 2/2014 | Pathak | A61B 5/1101 |
| | | | | 623/65 |
| 2015/0300394 | A1* | 10/2015 | Pathak | A47G 21/02 |
| | | | | 335/205 |
| 2016/0242679 | A1* | 8/2016 | Pathak | A61B 5/1101 |
| 2016/0246162 | A1 | 8/2016 | Niemeyer et al. | |
| 2016/0372004 | A1* | 12/2016 | Pathak | A61B 5/4836 |
| 2017/0020704 | A1 | 1/2017 | Wu et al. | |
| 2017/0055885 | A1* | 3/2017 | Shoeb | A61B 5/225 |
| 2017/0100272 | A1* | 4/2017 | Pathak | A61J 7/00 |
| 2017/0213145 | A1* | 7/2017 | Pathak | G06N 7/005 |
| 2017/0348127 | A1* | 12/2017 | Pathak | A61B 5/4082 |
| 2018/0014958 | A1* | 1/2018 | Pathak | A61H 1/00 |
| 2018/0031952 | A1 | 2/2018 | Niemeyer et al. | |
| 2018/0032159 | A1* | 2/2018 | Pathak | G06K 9/24 |
| 2018/0058536 | A1* | 3/2018 | Pathak | A61B 5/1114 |
| 2018/0064597 | A1* | 3/2018 | Pathak | A61H 1/008 |
| 2018/0311062 | A1* | 11/2018 | Pathak | A61H 1/00 |
| 2020/0085168 | A1* | 3/2020 | Pang | F16M 13/04 |

OTHER PUBLICATIONS

Office Action dated May 16, 2022, in corresponding Japanese Patent Application No. 2021-539506, 3 pages.
Office Action dated Apr. 14, 2022 in Chinese Application No. 201980061190.6 (w/partial English translation).

* cited by examiner

MOTION STABILIZING DEVICE FOR A COSMETIC APPLICATOR

FIELD

The present disclosure describes a device for reducing the movement of a cosmetic applicator caused by unintentional movements of a user.

BACKGROUND

Unintentional movements of the human body, or human tremors, can occur in individuals suffering from motion disorders or even healthy individuals. Due to these unintentional movements, a person may have difficulty in performing a task that requires care and precision, such as applying a cosmetic ingredient to a part of the body, such as the face or hands and feet.

Therefore, there is a need for a solution that allows application of a cosmetic ingredient that is compatible with the diverse and disposable nature of cosmetic applicators.

SUMMARY

In an embodiment, an apparatus is provided that stabilizes an applicator in response to the motion caused by a user, comprising: a receiver configured to be coupled with a cosmetic applicator; at least one sensor configured to detect a movement caused by a user; circuitry configured to determine a compensation movement to offset the detected movement; and at least one motion generation device embedded in the receiver configured to control a motion of the cosmetic applicator according to the determined compensation movement.

In an embodiment, the at least one motion generation device includes a combination of a Y-axis motive element and an X-axis motive element.

In an embodiment, the at least one motion generation device includes an electromagnetic positioner that includes a plurality of magnetic cores arrayed around a cavity that is filled with a magnetic fluid.

In an embodiment, the cosmetic applicator is any one of a mascara applicator, a nail polish applicator, and a lipstick applicator.

In an embodiment, the receiver includes reader circuitry configured to read data from circuitry embedded in the cosmetic applicator.

In an embodiment, the reader circuitry is configured to receive information of a particular type of the cosmetic applicator from the circuitry embedded in the cosmetic applicator.

In an embodiment, the reader circuitry is a radiofrequency identification (RFID) reader and the circuitry embedded in the cosmetic applicator is a RFID tag.

In an embodiment, the circuitry is configured to determine the compensation movement based on the received information.

In an embodiment, the circuitry is configured to determine an initial receiver angle based on the received information.

In an embodiment, the receiver is configured to be coupled with the cosmetic applicator via an adapter device.

In an embodiment, the device includes a handle portion that is separate from the receiver, and the receiver is configured to be set in any one of a straight position and an angled position with respect to the handle portion.

In an embodiment, a method is provided, implemented by an apparatus for reducing a motion caused by a user, the apparatus including a receiver configured to be coupled with a cosmetic applicator, the method comprising: detecting, by at least one sensor, a movement caused by a user; determining, by circuitry, a compensation movement to offset the detected movement; and controlling, via at least one motion generation device, a motion of the cosmetic applicator according to the determined compensation movement.

In an embodiment, the method further includes, reading, by reader circuitry included in the receiver, data from circuitry embedded in the cosmetic applicator.

In an embodiment, the method further includes receiving, by the reader circuitry, information of a particular type of the cosmetic applicator from the circuitry embedded in the cosmetic applicator.

In an embodiment, the method further includes determining the compensation movement based on the received information.

In an embodiment, the method further includes determining an initial receiver angle based on the received information.

BRIEF DESCRIPTION OF THE DRAWINGS

The patent or application file contains at least one drawing executed in color. A more complete appreciation of the embodiments and many of the attendant advantages thereof will be readily obtained as the same becomes better understood by reference to the following detailed description when considered in connection with the accompanying drawings, wherein.

DETAILED DESCRIPTION

The present disclosure describes a cosmetic applicator that minimizes unintentional movements by stabilizing an applicator for a user and is also designed to be flexible to different types of commercially available cosmetic applications.

Figure 1:
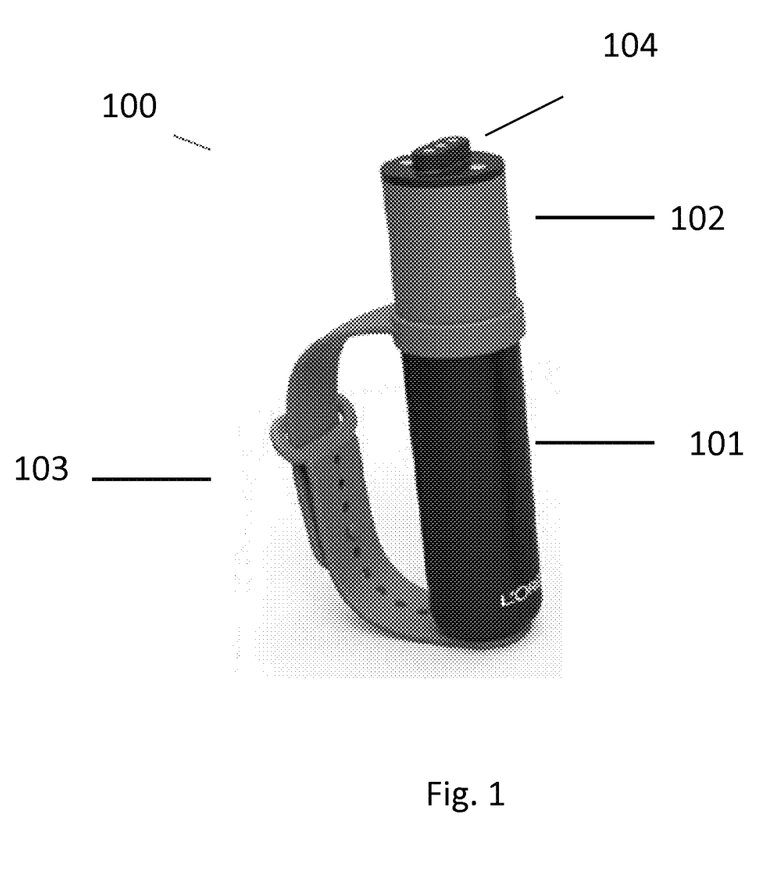
FIG. 1 shows a device which serves as a base unit for receiving a cosmetic applicator according to an embodiment.

FIG. 1 shows a device 100, which serves as a base unit for receiving a cosmetic applicator according to an embodiment. The device 100 includes a handle portion 101, a receiver portion 102 and a strap 103. The receiver portion 102 includes an interface 104, shown as a male connector that couples with a cosmetic applicator, which will be discussed in detail below. The receiver portion could be utilized for communication between the base unit and the applicator. The connection to an adaptor and/or an applicator could be accomplished with a mechanical coupling, such as screw-in or snap-fit, or it could be accomplished with magnets.

Figure 2:
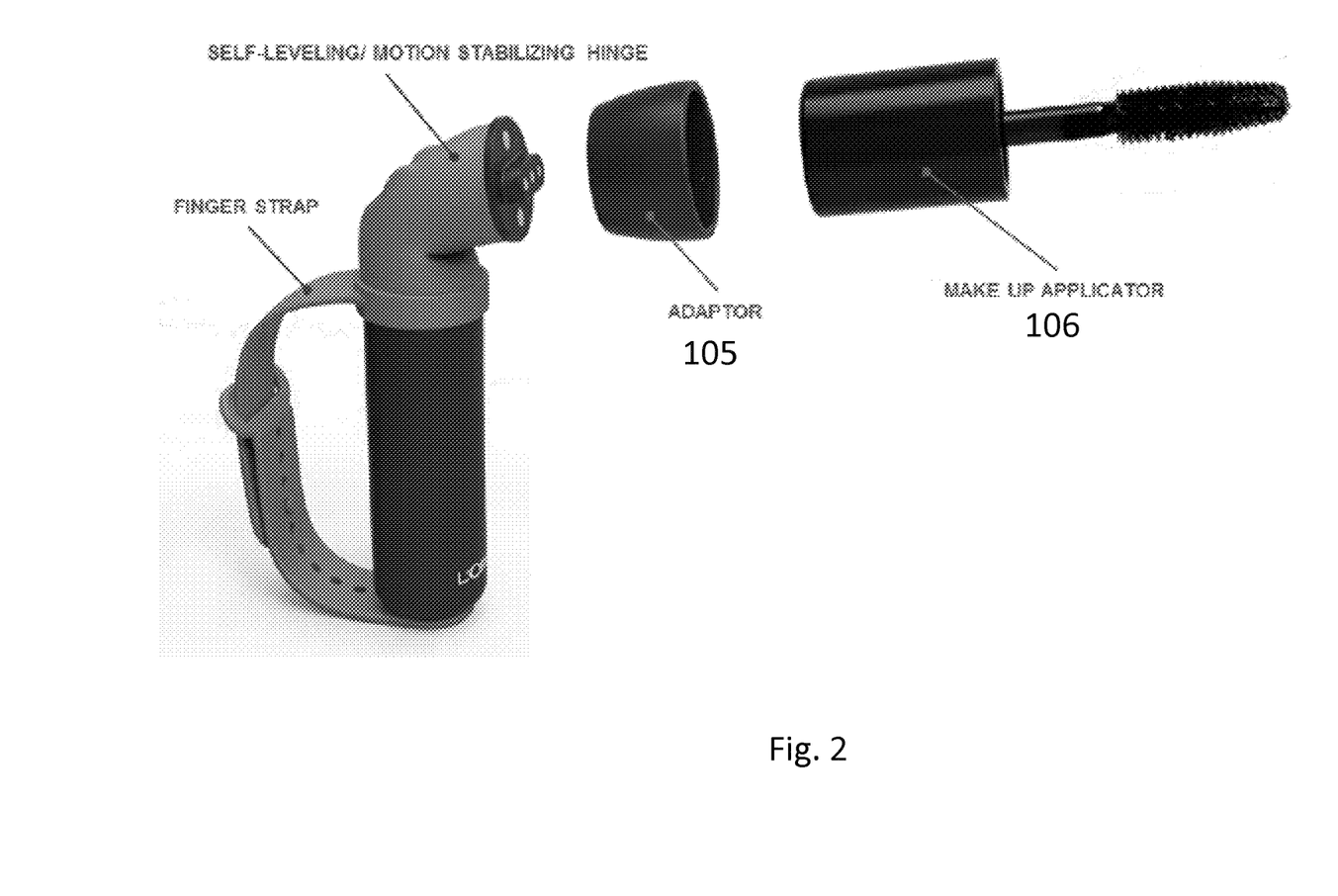
FIG. 2 shows how the device couples with an adaptor and a make-up applicator according to an embodiment.

FIG. 2 shows how the device 100 couples with an adaptor 105 and a make-up applicator 106. It can be seen that the adaptor fits over the exposed end of the receiver portion 102. The adaptor includes electrical mating connectors (a female connector—not shown) in a recessed portion to make contact with the electric interface of the receiver portion 101.

As shown in FIG. 2, the receiver portion 102 is configured to contort between an upright posture (as shown in FIG. 1) and an angled posture (as shown in FIG. 2). This is accomplished with a hinge mechanism contained inside the receiver portion 102. FIG. 2 shows that the hinge mechanism is a self-leveling/motion stabilizing hinge.

Figure 3A:
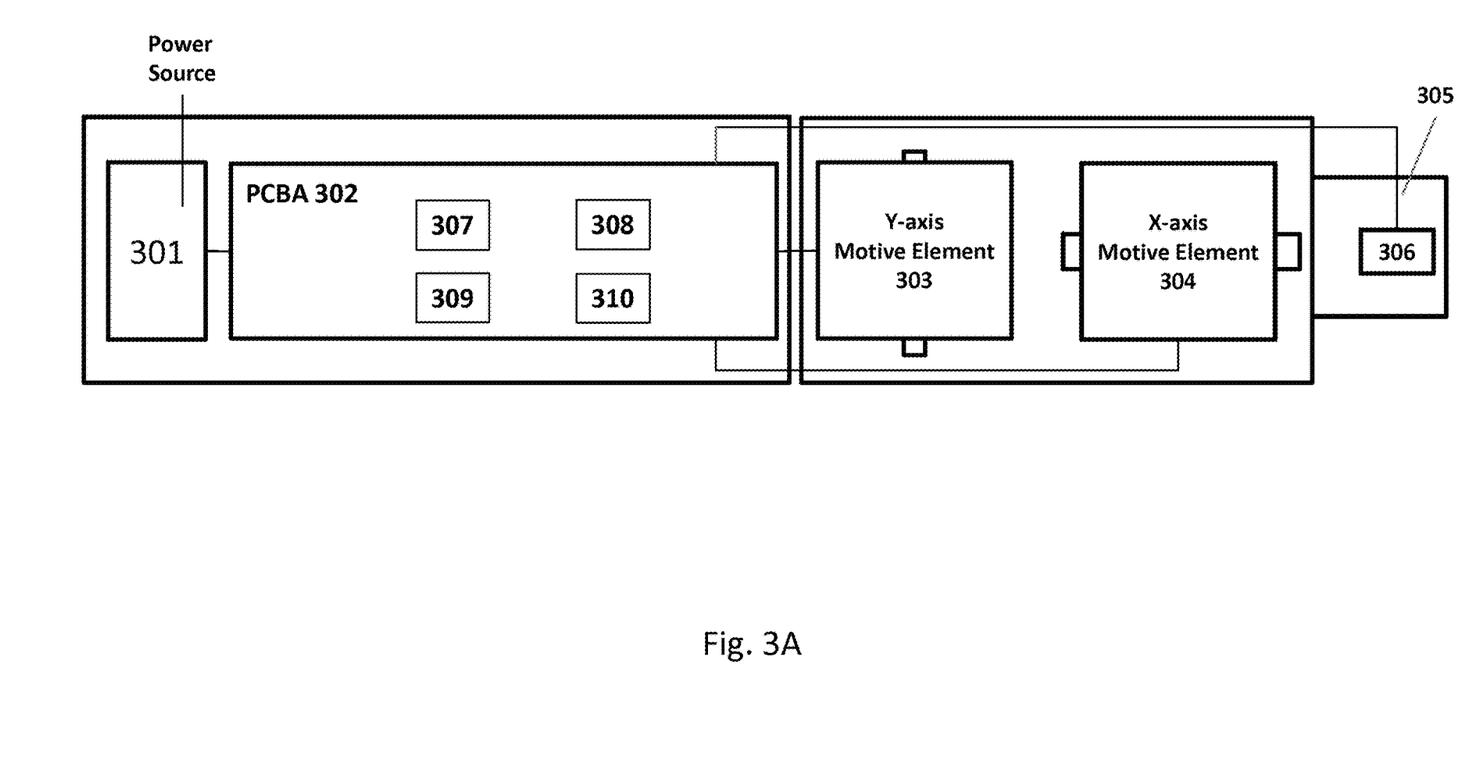
FIG. 3A shows a diagram of the internal components of device according to one embodiment.

FIG. 3A shows a diagram of the internal components of device 100 according to one embodiment. In the handle portion, the device includes a power source 301, which may be a battery or the like. The device includes a printed circuit board assembly (PCBA) 302, which may include positional sensor circuitry 307, reader circuitry 308, control circuitry 309, and communication interface 310, as understood in the art.

For instance, as the sensor circuitry 307, the PCBA may include at least one inertial sensor and at least one distributed motion sensor to detect unintentional muscle movements and measure signals related to these unintentional muscle movements that are created when a user adversely affects motion of the applicator. These sensors also detect the motion of the stabilized output relative to device. The control circuitry sends voltage commands in response to the signals to the motion generating elements (described below) to cancel the user's tremors or unintentional muscle movements. This cancellation maintains and stabilizes a position of the applicator, keeping it stable.

One of ordinary skill in the art readily recognizes that a system and method in accordance with the present invention may utilize various implementations of the control circuitry and the sensor circuitry and that would be within the spirit and scope of the present invention. In one embodiment, the control circuitry 309 comprises an electrical system capable of producing an electrical response from sensor inputs such as a programmable microcontroller or a field-programmable gate array (FPGA). In one embodiment, the control circuitry comprises an 8-bit ATMEGA8A programmable microcontroller manufactured by Atmel due to its overall low-cost, low-power consumption and ability to be utilized in high-volume applications.

In one embodiment, the at least one inertial sensor in the sensor circuitry is a sensor including but not limited to an accelerometer, gyroscope, or combination of the two. In one embodiment, the at least one distributed motion sensor in the sensor circuitry is a contactless position sensor including but not limited to a hall-effect magnetic sensor.

The system created by the combination of the sensor circuitry, the control circuitry, and the motion generating elements may be a closed-loop control system that senses motion and acceleration at various points in the system and feeds detailed information into a control algorithm that moves the motion-generating elements appropriately to cancel the net effect of a user's unintentional muscle movements and thus stabilize the position of the applicator. The operation and details of the elements of the control system and control algorithm are understood in the art, as described in U.S. PG Publication 2014/0052275A1, incorporated herein by reference.

The communication interface 310 may include a network controller such as BCM43342 Wi-Fi, Frequency Modulation, and Bluetooth combo chip from Broadcom, for interfacing with a network.

In the receiver portion of the device, there may be two motive elements to allow 3-dimensional movement of the receiver as anti-shaking movement. The two motive elements include a y-axis motive element 303 and an x-axis motive element 304, each being connected to and controlled by the PCBA 302. Each of the motive elements may be servo motors as understood in the art. The device further includes end effector coupling 305, which is configured to couple with the adaptor 105. The end effector coupling 305 may include a radiofrequency identification (RFID) reader 306, configured to read an RFID tag, which may be included with the applicator, as will be discussed below.

Figure 3B:
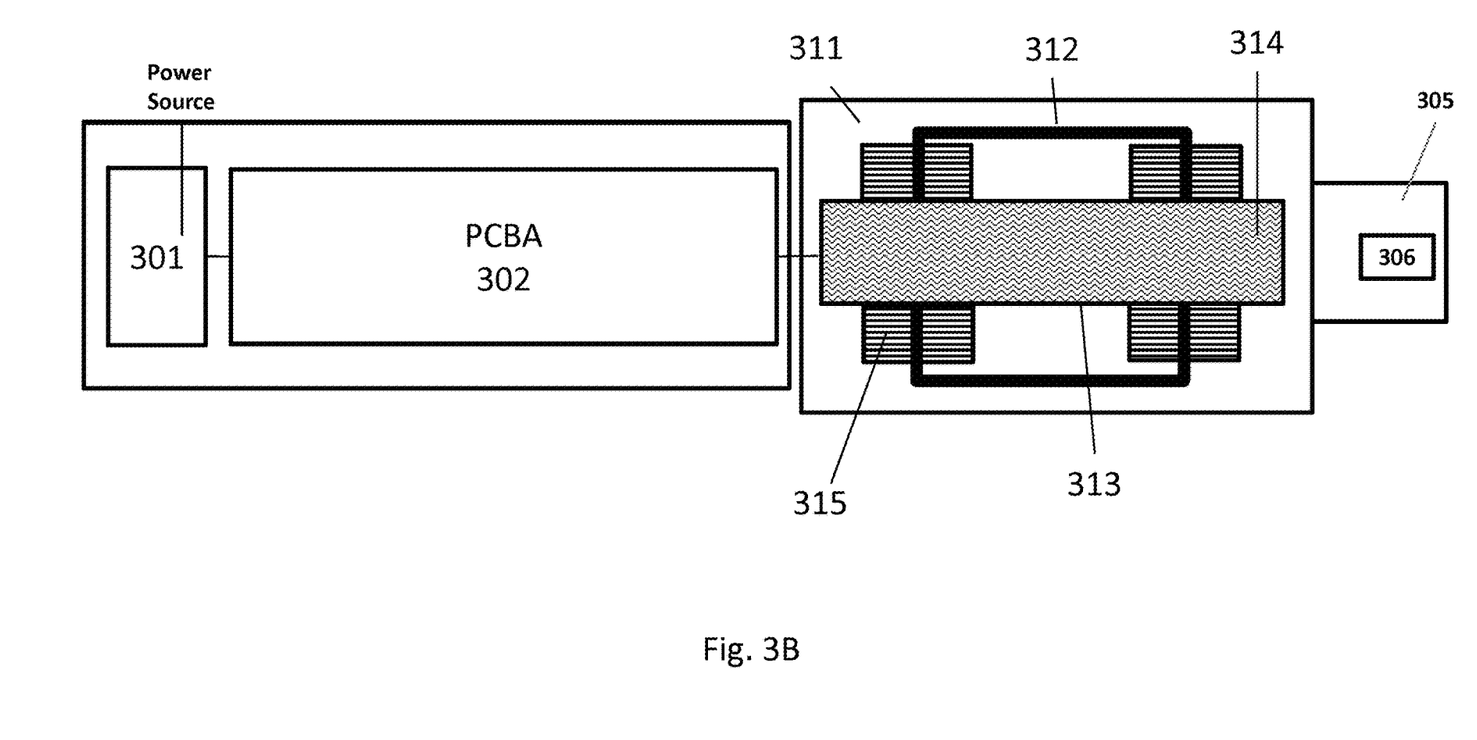
FIG. 3B shows a diagram of an alternative embodiment of the device in which the receiver portion includes an electromagnetic positioner instead of the motive elements shown in FIG. 3A.

FIG. 3B shows a diagram of an alternative embodiment of the device 100 in which the receiver portion includes an electromagnetic positioner 311 instead of the motive elements shown in FIG. 3A. The electromagnetic positioner 311 may include U-shaped magnetic cores 312 arrayed around a non-magnetic tube 313, which is filled with a magnetic fluid 314. Each of the magnetic cores has arm portions that are surrounded by windings 315. The magnetic cores may be controlled by the control circuitry in the PCBA 302 to act as a controllable active magnetic field-generating structure which is used to generate a variable magnetic field that acts upon the magnetic fluid, causing it to be displaced, thereby enabling the armature to be moved to a desired coordinate position and/or orientation. The details of implementing the electromagnetic positioner 311 may be found in U.S. Pat. No. 6,553,161, which is incorporated herein by reference.

Figure 4:
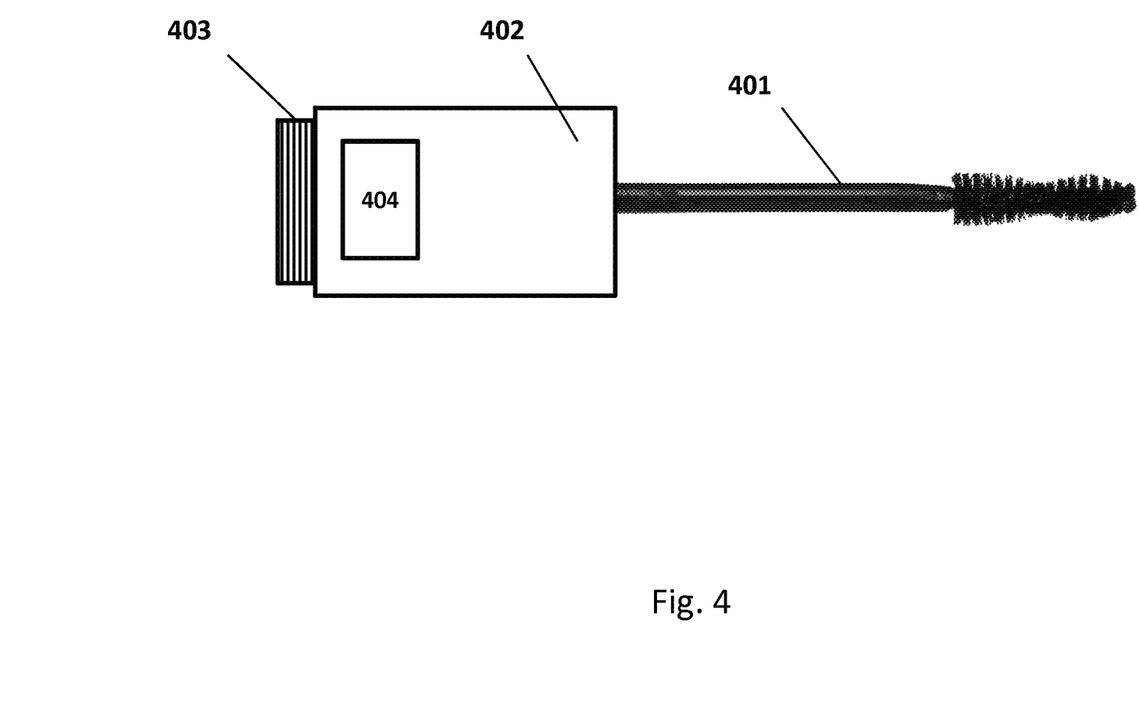
FIG. 4 shows the components of the makeup applicator according to an embodiment.

FIG. 4 shows the components of the makeup applicator 106. The applicator includes the applicator tool portion 401, which is shown as a mascara brush but it is not limited thereto and it may be any protruding or extending type of make-up tool, such as a lipstick applicator, a nail polish applicator, or the like. The applicator includes a base portion 402 which is coupled to the applicator tool portion 401. The connection between the base portion 402 and the applicator tool portion 401 may be permanent, or the tool portion 401 may be removable based any method known in the art (such as a screw coupling). The applicator further includes a receiver coupling element 403, which is shown as a male screw portion, but it is not limited thereto, and it may be any type of removeable attachment mechanism as understood in the art.

The applicator may further include an RFID tag 404, as known in the art, which may include information stored thereon. The information stored on the RFID tag may include information which identifies the specific type of applicator. Such information may be retrieved by the RFID reader 306 and then sent to the reader circuitry 309 and the control circuitry 308. This information may be used to make adjustments to the device based on the type of make-up applicator that is involved. For instance, different angles of orientation may be set depending on the type of make-up applicator that is being used. Alternatively, the weight of the applicator tool may be communicated to the control circuitry based on the information stored on the RFID tag, to allow precise control of the movement mechanism in response to any sensed shaking or tremors.

Figure 5A:
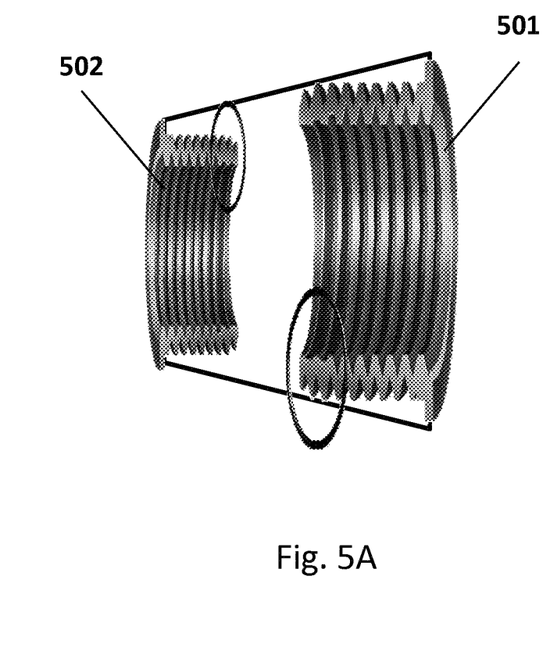
FIGS. 5A and 5B show examples of the adaptor according to different embodiments.
Figure 5B:
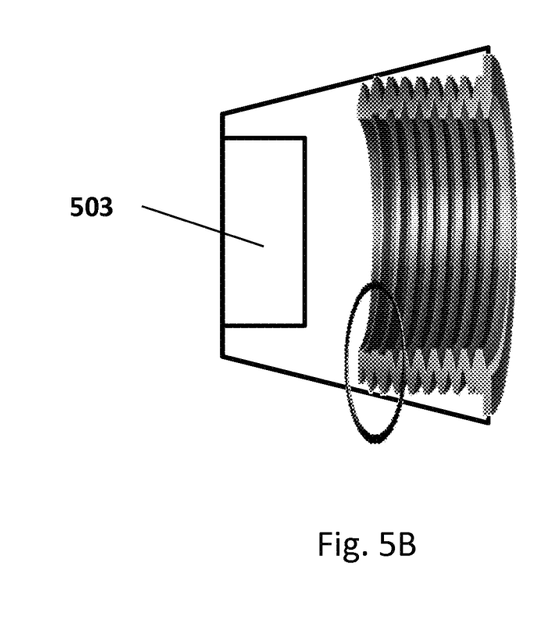

FIGS. 5A and 5B show examples of the adaptor 105. As seen in FIG. 5A, the applicator receiving end 501 may be a female threaded screw coupling having a size configured to receive the applicator, while the device receiving end 502 may be a female threaded screw coupling having a different size configured to attach to the coupling element 305 of the device 100. Alternatively, as shown in FIG. 5B, the device receiving end may include a magnet 503 for attaching to the device. While not shown a magnet or any other attaching means may be used for either end as necessary. Additionally, the adapter may not be necessary, and the coupling element 305 may be configured to directly attached to the applicator.

Figure 6A:
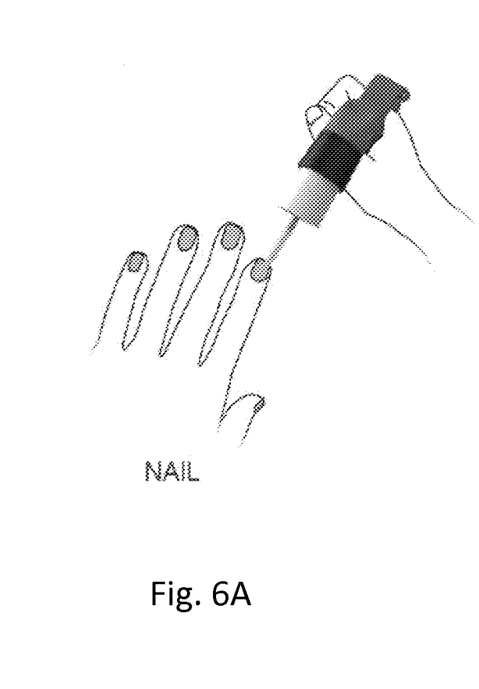
FIGS. 6A, 6B, and 6C show different examples of using the device with different applicators according to an embodiment.
Figure 6B:
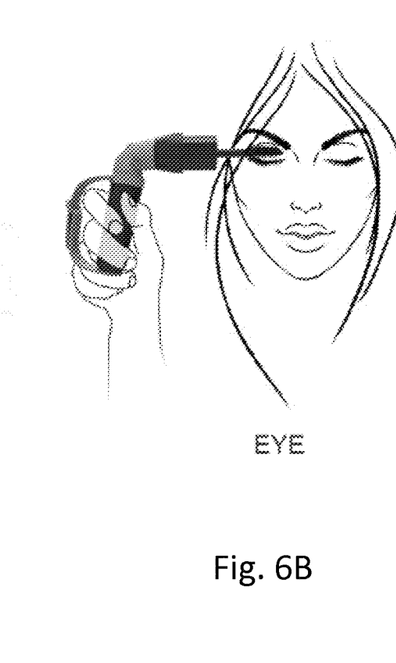
Figure 6C:
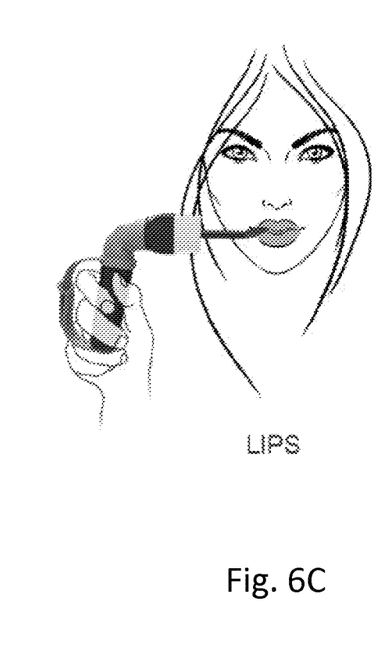

FIGS. 6A-6C show different example of using the device 100 with different applicators, such as a nail polish applicator in 6A, a mascara brush in 6B, and a lipstick applicator in 6C.

Figure 7A:
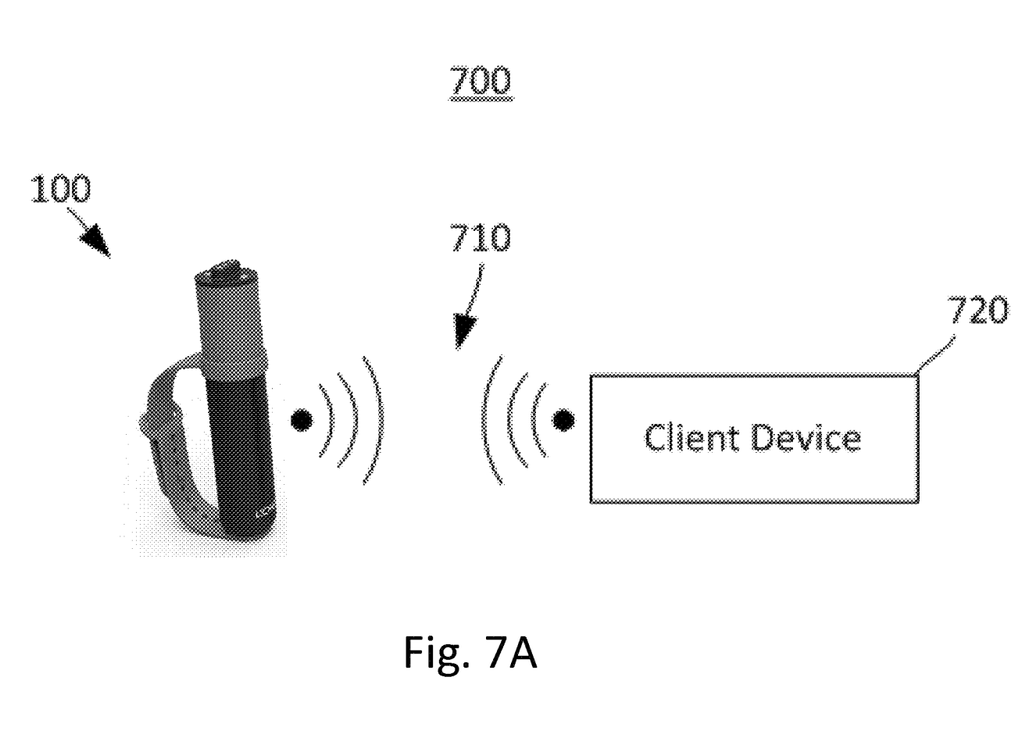
FIG. 7A shows a system that includes the device and a client device according to an embodiment.

FIG. 7A shows a system 700 that includes the device 100, as discussed above, and a client device 720. In an embodiment, the device 100 is in communication with the client device 720 with a wireless signal 710. In an embodiment, the client device 720 is configured to operate a software application or set of software modules to receive and send communications from and to the device 100. In an example, the software application can send a protocol or target profile to the device 100 for controlling the movement mechanism of a particular applicator, or for a particular user, as well as receive data from the device to track the usage and performance.

Figure 7B:
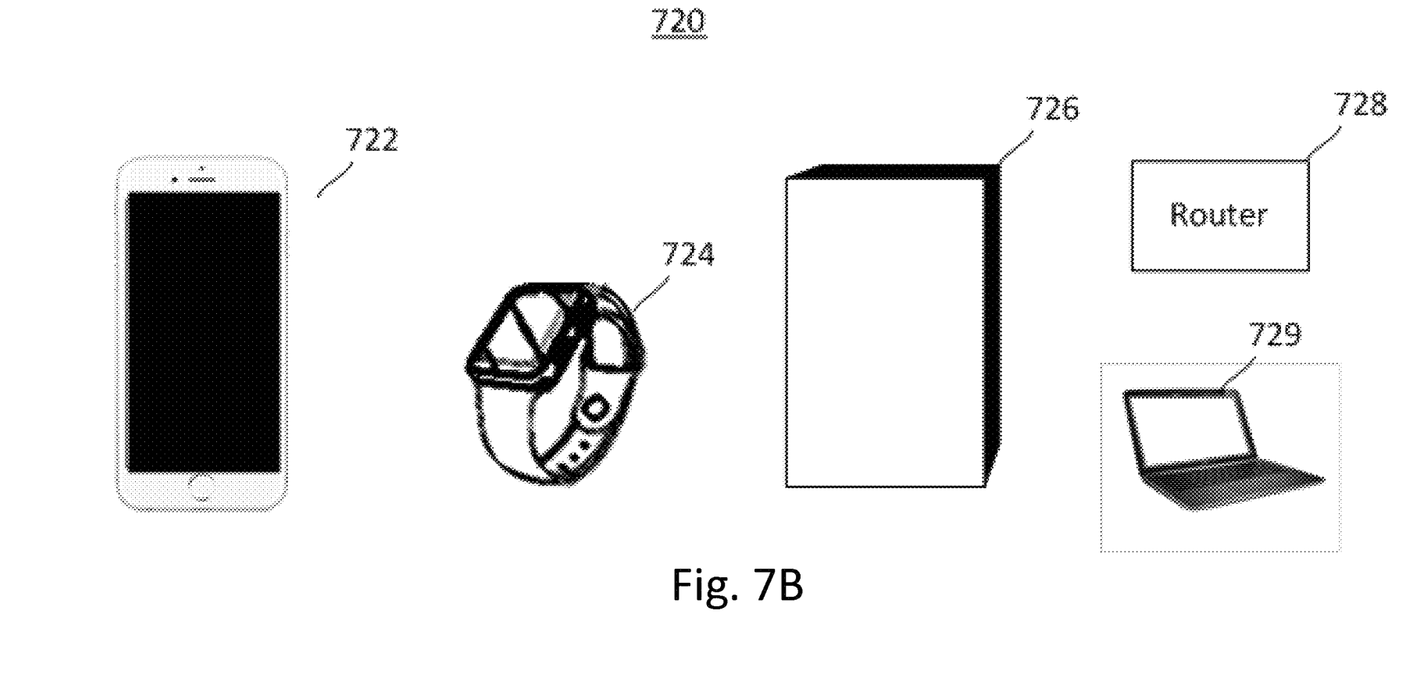
FIG. 7B shows different examples of the client devices according to an embodiment.

FIG. 7B shows different examples of the client devices 720 including, a mobile device 722, a wearable electronic device 724, a television or magic mirror 726, a network router 728, and a personal computer 729.

The wireless signal 110 can be any appropriate signal such as an electromagnetic signal including WiFi, Bluetooth, near-field, or any other signal such as optical, and acoustic. Each client device, including the appliance, may communicate with each other through an internet connection via an 802.11 wireless connection to a wireless internet access point, or a physical connection to the internet access point, such as through an Ethernet interface. Each connected device is capable of performing wireless communication with other devices, such as through a Bluetooth connection or other wireless means as well.

Figure 7C:
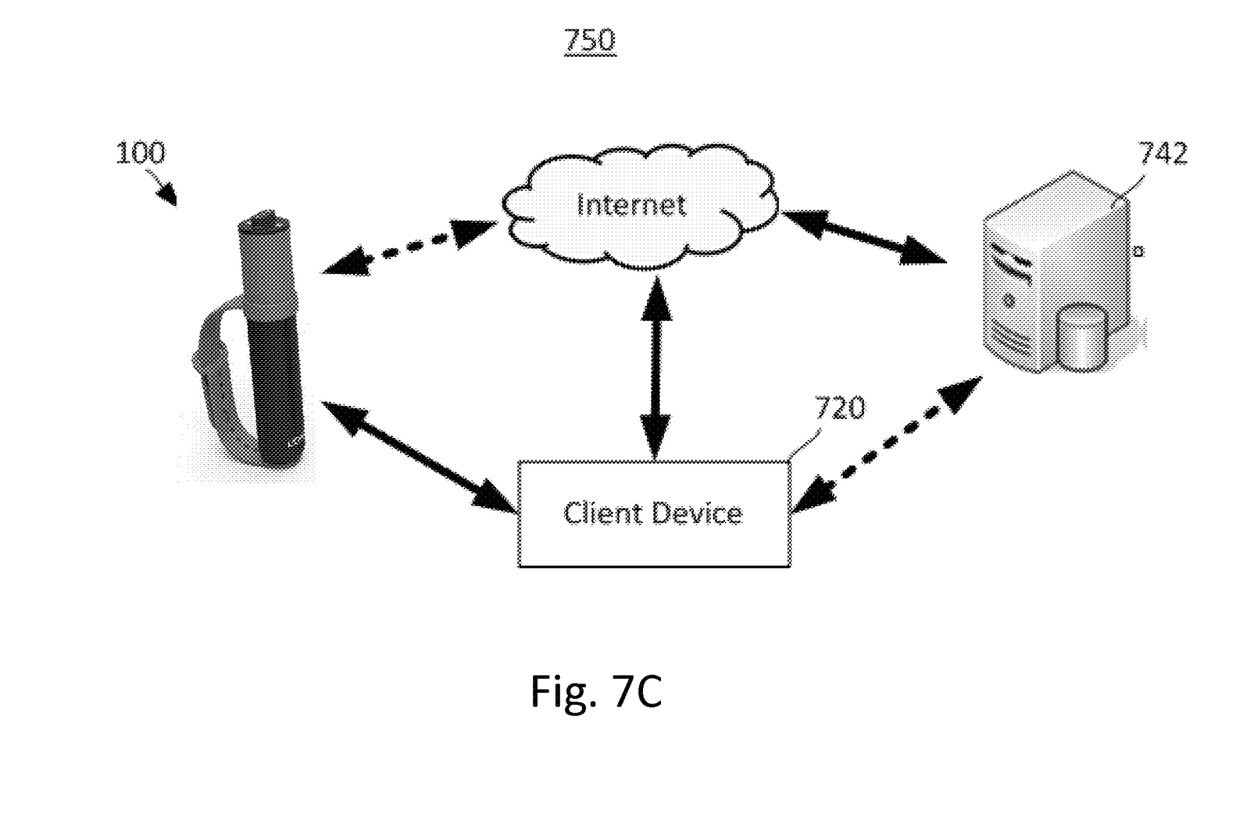
FIG. 7C is a diagram representing an example of a system to promote optimum performance of the device, according to an embodiment.

FIG. 7C is a diagram representing an example of a system 750 to promote optimum performance of the device 100, according to one example. The system 750 includes at least the device 100 and the client device 720. Optionally, the system 750 may further include one or more external servers 742 which are implemented as part of a cloud-computing environment and in communication with the system 750 through the Internet. The one or more external servers 742 can store user data, products such as protocols, algorithms, setting data, as well as other 3rd party services according to an example.

The client device 720 is configured, in one example, to collect information about a user's use of the device 100 and to provide output to the user. The operating system of the client device can have a user interface that is configured to perform multiple functions. In an aspect, the client device can be in communication with a network and enable the user interface access to the Internet as well as Internet of Things (IOT). As can be appreciated, the network can be a public network, such as the Internet, or a private network such as an LAN or WAN network, or any combination thereof and can also include PSTN or ISDN sub-networks. The network can also be wired, such as an Ethernet network, or can be wireless such as a cellular network including EDGE, 3G and 4G wireless cellular systems. The wireless network can also be WiFi, Bluetooth, or any other wireless form of communication that is known. In an example, the network can access a server hosting media, protocols, products, personal accounts, stored usage data, and other data related to the appliance, the brushheads, and skin care.

The user interface can display tutorials on how to use the device 100. The client device can create and download protocols for a routine or regimen that can be displayed on the user interface. The user interface can coach, track usage and compare the tracked usage to the protocol, the regimen, and the routine. The user interface can store the tracked usage of the device 100 in memory of the client device. The user interface can be used to make a purchase of any products related to the device 100. For instance, the client device can output recommendations on particular applicators to be used based on the desired results inputted by the user.

In addition, the user may connect the client device 720 with the device 100 over the wireless connection (such as the Bluetooth or Wi-Fi connection) to receive real-time feedback while using the device 100, or to record the usage of the device for later reporting or feedback.

The client device is configured to upload data regarding the user to an external system or server (such as a cloud-based system). Such data may include the user profile, amount of use of the device 100, or performance results when using the device 100. The client device can also provide an option to keep the user data anonymous.

Figure 8:
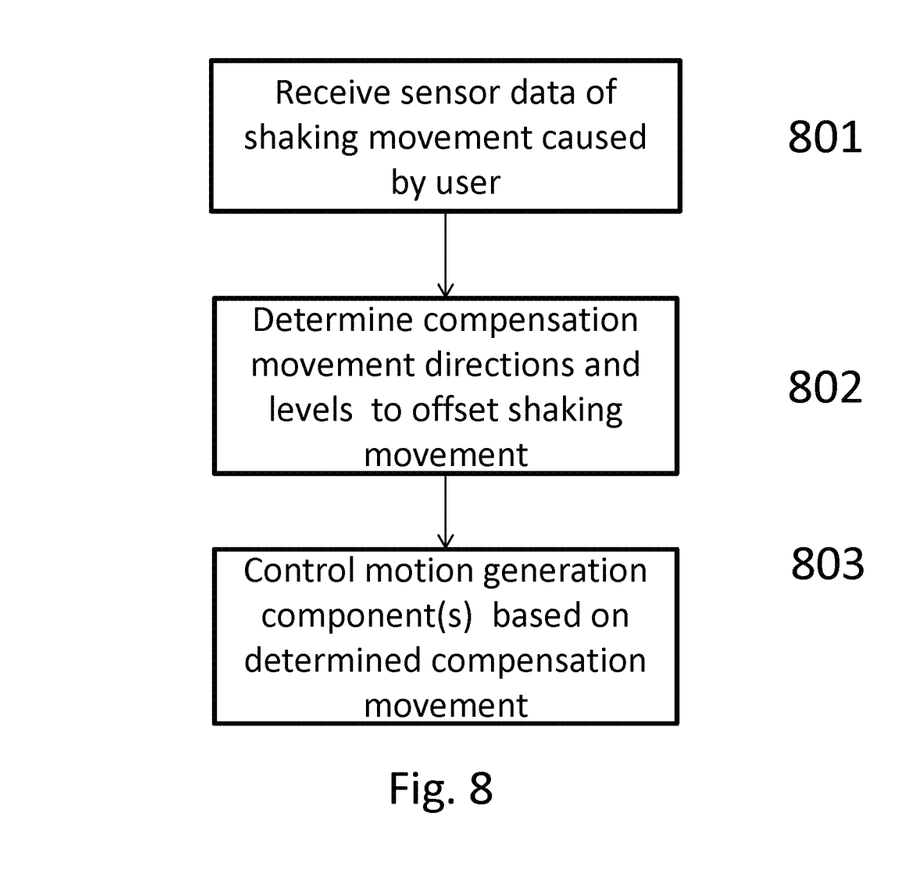
FIG. 8 shows a method performed by the circuitry of device according to an embodiment.

FIG. 8 shows a method performed by the circuitry of device 100. In step 801, the sensor circuitry receives data of a unintentional movement caused by the user. The movement may have particular characteristics or a profile that is distinguished from intentional natural movement caused by the user. In step 802, the control circuitry immediately begins to determine compensation movement direction and levels (which may be in the form of vectors) to offset the movement. This may be determined by recognizing a pattern in the movement, and then determining a patterned compensation response movement that will match the phase of the shaking movement. In step 803, the control circuitry then sends control signals to the motion generation components based on the determined compensation movement.

Obviously, numerous modifications and variations of the present invention are possible in light of the above teachings. It is therefore to be understood that within the scope of the appended claims, the invention may be practiced otherwise than as specifically described herein.

What is claimed is:

1. An apparatus that stabilizes a cosmetic applicator in response to a movement caused by a user, comprising:
   a power source;
   a receiver being configured to be coupled with a cosmetic applicator that is one of a mascara applicator, a nail polish applicator, and a lipstick applicator and that stores information on a type of cosmetic applicator;
   at least one sensor configured to detect the movement caused by the user;
   processing circuitry configured to determine a compensation movement to offset the detected movement; and
   a motion generation device embedded in the receiver configured to control a motion of the cosmetic applicator according to the determined compensation movement, wherein the receiver includes a radiofrequency identification (RFID) reader that reads data from an RFID tag that is included on the cosmetic applicator and receives the information that indicates the type of the cosmetic applicator, as one of the mascara applicator, the nail polish applicator, and the lipstick applicator, from the data read from the cosmetic applicator, and the processing circuitry is configured to determine the compensation movement based on the received information, wherein the apparatus includes a handle portion that is separate from the receiver, and the receiver includes a hinge mechanism that is configured to move the receiver between a straight position and an angled position with respect to the handle portion, and the processing circuitry is configured to determine an initial receiver angle based on the type of the cosmetic applicator included in the received information.

2. The apparatus according to claim 1, wherein the at least one motion generation device includes a combination of a first motive element disposed along a first axis and a second motive element disposed along a second axis that is perpendicular to the first axis.

3. The apparatus according to claim 1, wherein the motion generation device includes a plurality of magnetic cores arrayed around a tube that is filled with a magnetic fluid, the magnetic cores being controlled by the processing circuitry to act as a controllable active magnetic field-generating structure which is used to generate a variable magnetic field that acts upon the magnetic fluid, causing it to be displaced, thereby enabling an arm portion of each magnetic core to be moved to a desired coordinate position and/or orientation.

4. The apparatus according to claim 1, further comprising an adapter device, and wherein the receiver is configured to be coupled with the cosmetic applicator via the adapter device.

5. A method, implemented by an apparatus, for reducing a movement caused by a user, the apparatus including a power source, a receiver being configured to be coupled with a cosmetic applicator that is one of a mascara applicator, a nail polish applicator, and a lipstick applicator and that stores information on a type of cosmetic applicator, at least one sensor, processing circuitry, radiofrequency identification (RFID) reader, and a motion generation device, the method comprising:

detecting, by the at least one sensor, the movement caused by the user;

determining, by the processing circuitry, a compensation movement to offset the detected movement; and controlling, via the motion generation device, a motion of the cosmetic applicator according to the determined compensation movement, wherein the method further includes:

reading, by the RFID reader, data from an RFID tag that is included on the cosmetic applicator and receiving the information that indicates the type of the cosmetic applicator, as one of the mascara applicator, the nail polish applicator, and the lipstick applicator, from the data read from the cosmetic applicator, and determining, by the processing circuitry, the compensation movement based on the received information, wherein the apparatus includes a handle portion that is separate from the receiver, and the receiver includes a hinge mechanism that is configured to move the receiver between a straight position and an angled position with respect to the handle portion, and the method further includes determining an initial receiver angle based on the type of the cosmetic applicator included in the received information.

* * * * *